United States Patent [19]

Kompanek

[11] 4,193,010
[45] Mar. 11, 1980

[54] SENSOR DEVICE USING PIEZOELECTRIC COATING SUBJECTED TO BENDING

[75] Inventor: Harry W. Kompanek, Santa Barbara, Calif.

[73] Assignee: Essex Transducers Corporation, Carpinteria, Calif.

[21] Appl. No.: 889,997

[22] Filed: Mar. 24, 1978

Related U.S. Application Data

[63] Continuation-in-part of Ser. No. 749,132, Dec. 9, 1976, abandoned.

[51] Int. Cl.² ............................................. H01L 41/10
[52] U.S. Cl. .................................... 310/330; 310/324; 310/321; 310/358
[58] Field of Search ............... 310/311, 357, 358, 359, 310/321, 322, 324, 323, 330; 340/234–236, 244 R; 73/DIG. 4, 290 V, 398 R, 88.5 R, 432 PS, 23, 28

[56] References Cited

U.S. PATENT DOCUMENTS

| | | | |
|---|---|---|---|
| 3,638,052 | 1/1972 | Massa | 310/324 |
| 3,745,384 | 7/1973 | Blanchard | 310/324 |
| 3,815,129 | 6/1974 | Sweany | 310/324 X |
| 3,948,089 | 4/1976 | Shaw | 310/328 |
| 4,019,072 | 4/1977 | Mifune et al. | 310/338 X |

OTHER PUBLICATIONS

Brushed–on Piezoelectric Transducers by J. G. Martner, *Ultrasonics*, vol. 7, No. 4, Oct. 1969, pp.234–237.

*Primary Examiner*—Mark O. Budd
*Attorney, Agent, or Firm*—Anthony J. Criso

[57] ABSTRACT

A sensor device having a vibratable surface which can be exposed to various materials and used to determine the presence thereof is disclosed. The device includes a sandwich structure comprising a substrate coated with a piezoelectric material, a pickup electrode joined to the piezoelectric and a drive electrode also joined to the piezoelectric. The piezoelectric material is applied to the substrate as a slurry and when dried forms a ceramic coating which is chemically bonded to the substrate. The sensor is electrically driven to vibrate and depending upon the absence or presence of the material to be detected a characteristic vibrational frequency or amplitude of the sensing surface is observed to indicate contact with such material. Various embodiments are discussed including a rectangular configuration which is cantilevered from a support base and a circular configuration which is held circumferentially by the support base.

6 Claims, 11 Drawing Figures

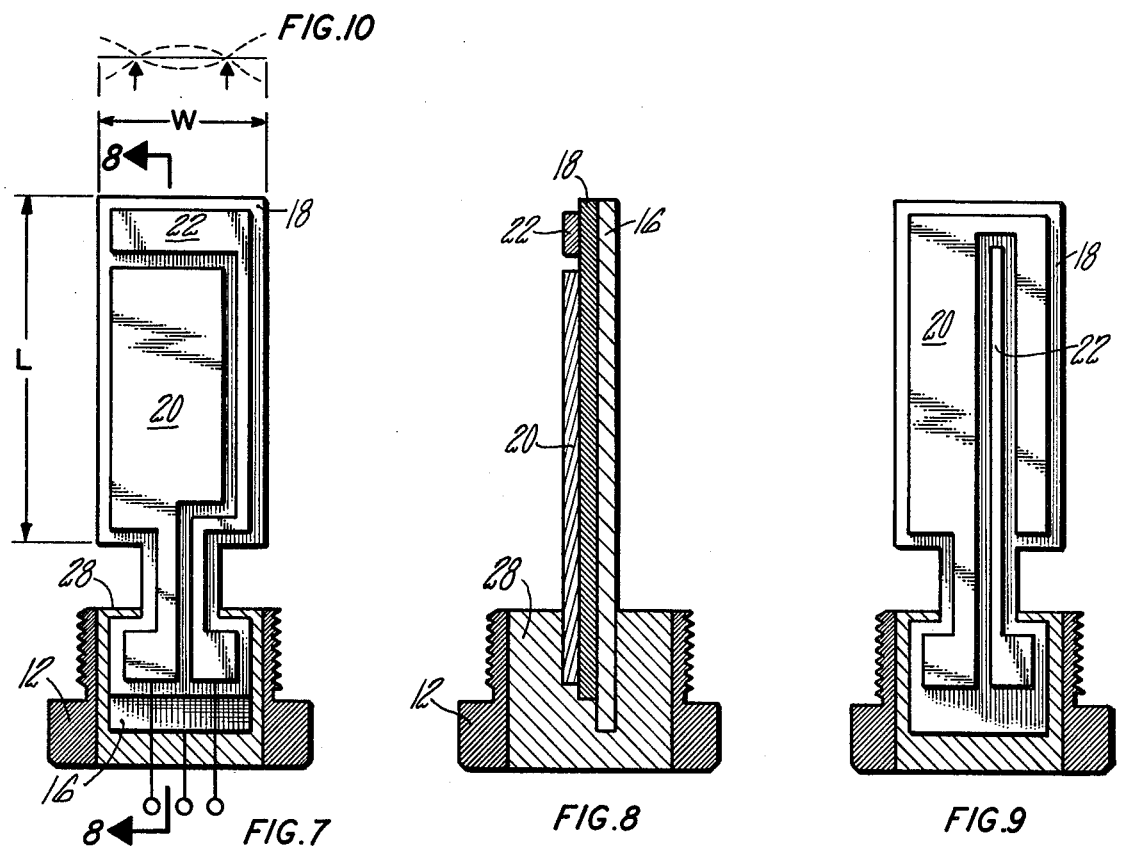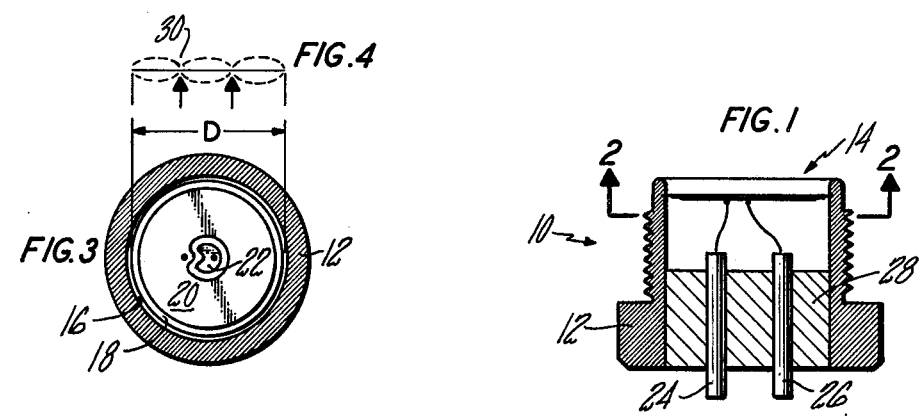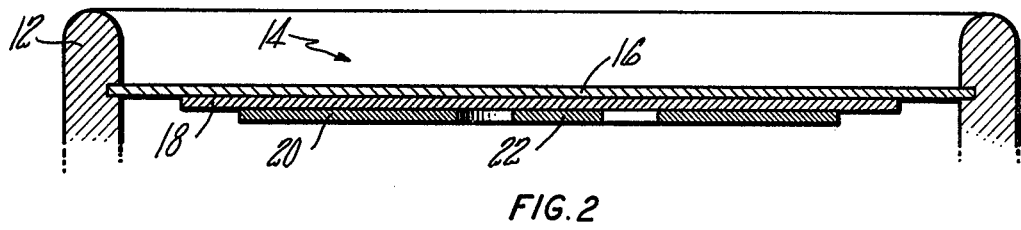

SENSOR DEVICE USING PIEZOELECTRIC COATING SUBJECTED TO BENDING

CROSS REFERENCE TO RELATED APPLICATION

This patent application is a continuation in part of application Ser. No. 749,132 which was filed on Dec. 9, 1976, now abandoned.

BACKGROUND OF THE INVENTION

The present invention relates to sensors and more particularly to simple sensors having piezoelectric material in the transducer.

Considerable effort has gone into the development of mechanisms which function to measure or locate the level of a material in a container. Typical of such devices is the apparatus taught by Mongan in U.S. Pat. No. 3,010,318 entitled Method and Apparatus for Measuring Liquid Levels. The essence of the Mongan device includes a transmitter and a receiver with an interconnecting waveguide running therebetween such that ultrasonic waves produced at the transmitter are passed through the waveguide to the receiver. In operation, the waveguide is positioned to pass through the liquid vapor interface and since the impedance of the waveguide will vary depending upon the amount of surface in contact with the liquid thereby affecting the amount of transmitted power which reaches the receiver, with suitable calibration of the device of the signals arriving at the receiver can be converted to liquid level position. This relatively large device uses multiple transducers, is cumbersome and expensive for many applications.

In the Fetal Heart Transducer described by J. R. Richards in U.S. Pat. No. 3,379,901, an apparatus comprising two circular transducers mounted concentrically is described. One transducer acts as a transmitter and the other as a receiver in the transmission of sonic energy through liquids to investigate a fetal heart by studying the doppler shift in the reflected waves. The Richards' apparatus comprises two concentric piezoelectric crystals which are located in a disc assemblage and are carefully isolated physically and electrically from each other.

U.S. Pat. No. 3,625,058 to Endress et al liquid is present. Two parallel vibrator rods are induced to vibrate by a piezoelectric transducer and a second transducer senses the rod motion and provides an output signal which is proportional to the amplitude of such motion. When the mechanism is immersed in a liquid the vibrational frequency changes and is sensed in the receiving transducer. Another transducer containing sensing apparatus is disclosed by Samuel et al who describe a transducer for sensing the presence of a liquid in U.S. Pat. No. 3,825,025. The basic apparatus comprises two piezoelectric elements which are spaced apart from one another and means for inducing ultrasonic vibrations in one of the elements. The coupling between the two piezoelectric elements is a function of the level of liquid which is present in the physical space left between the two transducers and which is oriented in a vertical direction so that with suitable calibration the system can be used to determine fluid level.

A simple rugged device which can be built inexpensively and perform with great reliability such as that demanded for liquid level sensing in automobile applications is needed.

SUMMARY OF THE INVENTION

A primary object of the present invention is to sense the level of fluid such as a liquid or dry materials such as pellets or powders and to sense an interfacing with solids such as the touch of a finger or the accumulation of frost on a surface.

According to the present invention, a sensing apparatus is formed from a sandwich element having a layer of piezoelectric material which responds to an electrical input delivered through a drive electrode to induce resonant vibration in the sandwich thereby causing stress in the piezoelectric material and an electrical response which is sensed in a pickup electrode, and an electronic circuit which both provides the electrical input and processes the electrical response to discern changes in the resonant frequency or vibration amplitude of the apparatus due to interaction between the sandwich element and the adjacent environment. The sandwich element comprises a substrate of conductive material with a coating of piezoelectric material chemically bonded thereto, a drive electrode of relatively large area attached to the piezoelectric and a pickup electrode also attached to the piezoelectric but spaced apart from the drive electrode. The piezoelectric material is applied to the substrate in the form of a slurry and dried to form a hard ceramic coating which chemically bonds to the substrate. The electronics comprises a simple self-oscillating circuit which includes an amplifier, a voltage level sensor, a lamp switch and a warning light, or a self-oscillating circuit which includes self-oscillating means and frequency sensitive detection means, or an external driving oscillator circuit which includes a frequency modulated oscillator controlled with a sweeping oscillator.

The present invention is characteristically a simple apparatus which is compact, rugged and inexpensive to manufacture. The sensing element can be either a cantilevered blade or a disc which is held circumferentially. The apparatus can be assembled with several sensors which use some common electronics and some individual electronics. The sensor is subjected to bending mode resonances which provide the largest mechanical displacement and in turn the largest electrical output. Also, the use of piezoelectric coatings allows the resonance range to be stuffed into the ultrasonic and near ultrasonic frequencies.

The foregoing and other objects, features and advantages of the present invention will become more apparent in the light of the following detailed description of preferred embodiments thereof as discussed and illustrated in the accompanying drawing.

BRIEF DESCRIPTION OF THE DRAWING

FIG. 1 is a cross section through a disc sensor embodiment in accordance with the present invention;

FIG. 2 is an enlarged view of the disc element of the sensor;

FIG. 3 is a view of the bottom surface of the disc element;

FIG. 4 is a sketch of the vibrational mode of the disc element;

FIG. 7 is a front view of a blade sensor in accordance with the present invention with the base element shown in section;

FIG. 8 is a side view of the apparatus shown in FIG. 4;

FIG. 9 is an alternate embodiment of a blade sensor;

FIG. 10 is a sketch of the vibrational mode of the blade element; and

DESCRIPTION OF PREFERRED EMBODIMENTS

Figure 5:
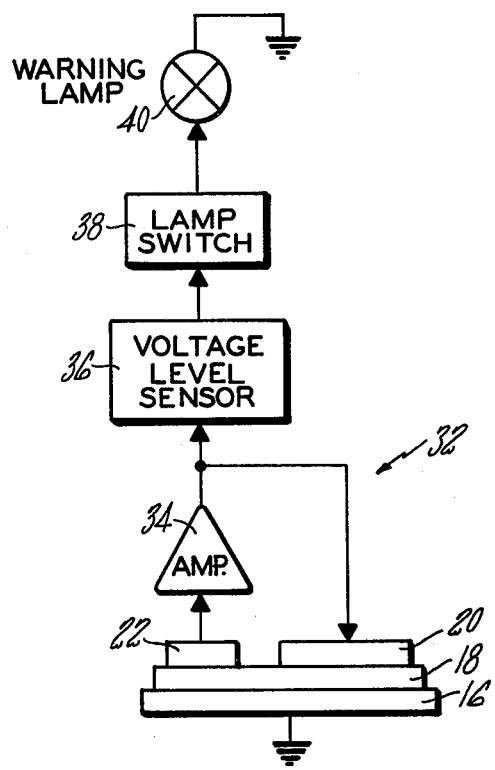
FIG. 5 is a simplified wiring schematic showing a self-oscillating electronic circuit useful with the level sensor.

One of the very practical applications of the sensor devices in accordance with the present invention is as a level sensor for fluids in the various liquid systems in an automobile. In such an application, the sensor which includes a mechanical element having a vibratory resonance in the ultrasonic range is placed at the desired lowest level position in, for example, the brake fluid system. If the sensor is exposed to liquid a characteristic electric output signal is observed, however, if the fluid drops below the position of the sensor, the acoustic load which the fluid would otherwise be exerting on the sensor is removed and is detected as a change in either the resonant frequency or the vibration amplitude of the output signal from the sensor depending on the type of electronic circuit used.

One configuration of a sensor in accordance with the present invention which uses an active element in the shape of a disc is shown in FIGS. 1-3. A sensor 10 is formed from a circular base 12 and a disc assembly 14. The disc assembly comprises a substrate 16, a layer 18 of piezoelectric material, a drive electrode 20 and a pickup electrode 22. A first conductor 24 is connected to the drive electrode and a second conductor 26 is connected to the pickup electrode, each conductor being electrically isolated from the other and passing through a sealant 28 which closes off one end of the circular base and holds the conductors in place. A suitable selection of the materials and shape of the components comprising the disc assembly allows the apparatus to have a bending mode characteristic such as is shown in FIG. 4. A nodal ring 30 located in the disc assembly defines the preferred sites for the electrical connection between the conductors and the disc assembly. These connection points are preferred since they do not experience the extensive cyclic displacement which is experienced at other locations on the disc. As a practical matter, the drive electrode is located at the outside edge of the nodal ring and the pickup electrode is located at the inside edge of the nodal ring for the sensor shown in FIG. 3.

For one of the preferred embodiments of the invention, a hard ceramic powder was formed by mixing lead zirconate and lead titanate in the respective percentages by weight of fifty two and forty eight and then firing the mixture. A highly acid solution comprising phosphoric acid, chromic acid, gluconic acid and zinc oxide was then admixed with the ceramic powder. The gluconic acid functions as a plasticizer and a wetting agent and allows the slurry to be more dense. The acid solution is characteristically at about 0.85 pH under room temperature conditions and as long as the ceramic powder is in the form of finely classified particles the slurry is highly dense.

The dense slurry was applied to a stainless steel substrate by a flow process although dip and spray techniques are feasible, and then cured at a temperature of approximately three hundred seventy five degrees Farenheit for approximately one-half hour. The curing process reduced the slurry to a hard ceramic which was chemically joined to the substrate as an extremely hard coating. The coating could not be removed easily although with mechanical processes such as scraping the surface of the substrate was found to be very much etched. After the slurry was cured and the coating formed, the coating was polarized with a direct current voltage of about fifty volts per unit of coating thickness.

The precise chemical structure of the material in the transition zone from the substrate to the ceramic coating is not known with any certainty although the ceramic is definitely chemically bound to the substrate. According to one accepted rationale, the lead zirconate and lead titanate interbond with the phosphate and chromate materials to form a very complex phosphate-chromate compound which is piezoelectric in nature. Probably what occurs is the phosphates interact with the stainless steel surface directly and attach to the substrate in a manner which allows some lead zirconate and lead titanate particles to find their way into the locations at which the acid interacts intimately with the substrate. This transition zone is also intimately interconnected with the complex phosphate-chromate compound described previously and consequently the entire region immediately adjacent to the substrate right through to the ceramic coating is to some degree piezoelectric in nature.

The actual piezoelectric activity for the slurry is controlled to a large degree by the pH of the acid solution in the slurry formation, the higher the pH of the acid the lower the dielectric constant and resistivity of the slurry. This observation suggests that the phosphate itself is to a large degree piezoelectric although not nearly as piezoelectric as the lead zirconate-lead titanate powder per se.

Evidently the phosphate adds substantially to the piezoelectric activity of the signal generator manufactured in accordance with the present invention and the reason the slurry chemically attaches so rigidly to the stainless steel substrate is due to the phosphate-chromate chemical activity of the slurry. In effect, the slurry is causing an etching effect on the substrate and the phosphate ceramic coating is intimately formed at the interface of the substrate resulting in a very strong bond. For additional discussion of coating compositions, deposition processes, and resulting articles see U.S. Pat. No. 4,056,654 which issued on Nov. 1, 1977 to Harry W. Kompanek, the substance and disclosure of which is hereby incorporated by reference into the present application.

In addition to the basic mechanical apparatus which has been described, suitable electrical circuitry is necessary to an overall sensor device. One such circuit which includes a warning lamp such as would be located on the dashboard of an automobile is shown in FIG. 5. In this circuit, the sensor is placed in a feedback loop 32 with appropriate gain, frequency response, and phase shift so that oscillation of the feedback loop occurs under stable loading conditions on the sensor. Ordinarily the system is arranged to oscillate whenever the sensor is exposed to air for example and to cease oscillating when exposed to a fluid although these conditions can be reversed in preferred circumstances.

In operation of the self-oscillating system shown in FIG. 5, the gain, response and phase shift of the feedback loop are such that oscillation occurs in the circuit when the sensor is exposed only to air; no oscillation occurs when the sensor is exposed to a liquid. A feedback amplifier 34 drives a voltage level sensor 36 which determines the level of the output voltage due to the oscillation condition. The voltage sensor controls a lamp switch 38 which in turn activates a warning lamp 40 for those conditions when the fluid is not in contact with the sensor.

Figure 6:
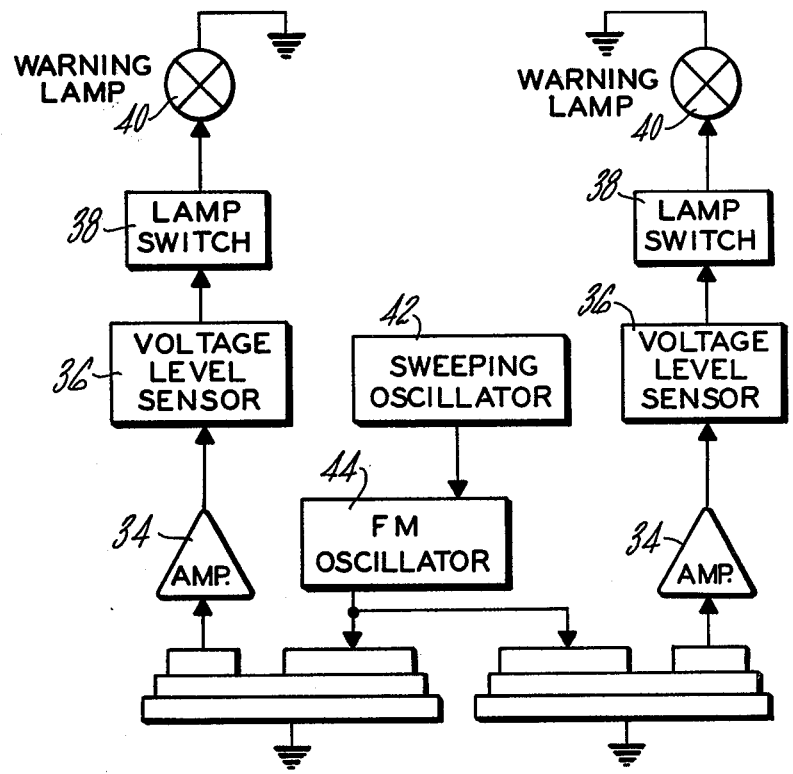
FIG. 6 is a simplified wiring diagram of an external driving oscillator circuit which is useful with the present invention.

In some applications multiple sensor units are used in combination and a single drive oscillator powers several sensors. This results in less critical individual amplifier circuits since the amplifiers do not have to be tuned. Such a circuit is shown in FIG. 6 wherein the output from a sweeping oscillator 42 causes a frequency modulated oscillator 44 to undergo a range of periodic frequency changes in output signals which includes the resonant frequency of the sandwich under no load conditions and excludes the loaded resonance. The frequency range over which the signals from the sweeping oscillator is modulated is made sufficient to include the range of resonant frequencies which will occur when the sensor is subject to an error load, the range being due to variations in such considerations as manufacturing tolerances and temperature, etc. Although the externally driven system in FIG. 6 is described for use with multiple sensors, the concept is applicable to a single sensor device.

Figure 11:
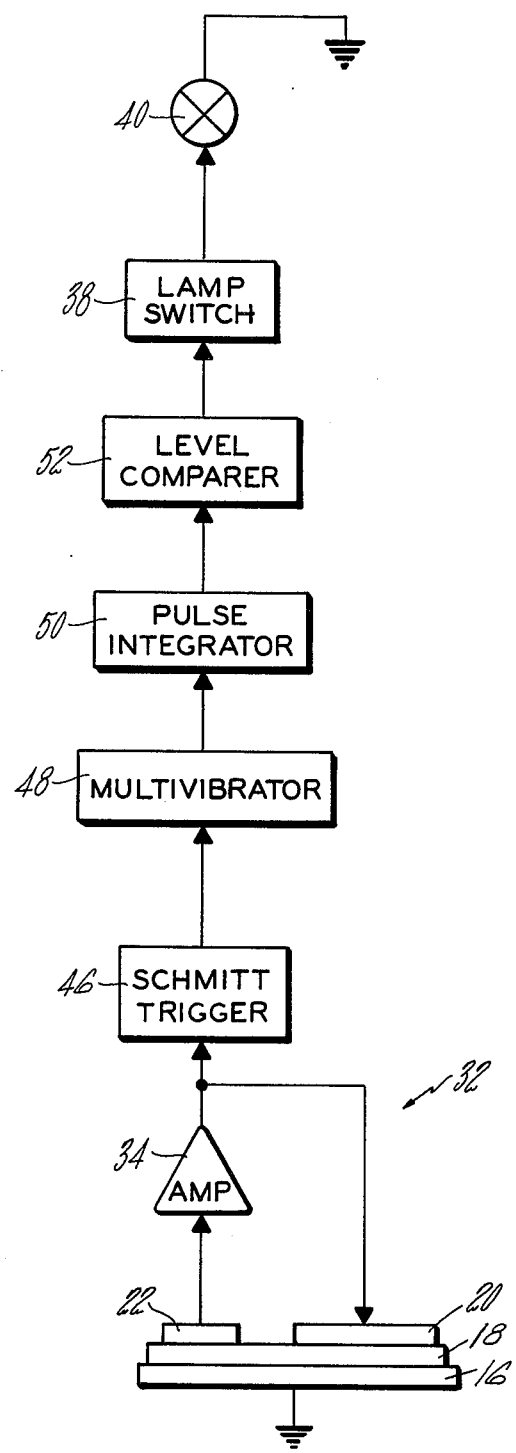
FIG. 11 is a simplified wiring diagram showing an alternate self-oscillating electronic circuit.

An alternative approach to the externally driven frequency-sensitive system is shown in FIG. 11. The circuitry required does not include the sweeping oscillator 42 or the frequency modulated oscillator 44 and is therefore simpler and less expensive. The output from the feedback loop 32 is passed through a Schmitt trigger 46 for the purpose of squaring up the pulse profile. These signals are then used to trigger a one shot multivibrator 48 to produce pulses of a uniform width and amplitude. The pulses are next passed through a pulse integrator 50 which adds the individual pulses to form a continuous signal level which increases with increasing pulse rate and decreases with decreasing pulse rate and which is matched against a reference voltage in a level comparer 82. In those circumstances in which the comparer determines that the output from the pulse integrator is high, which condition occurs when the vibration frequency is above a predetermined value as is the case when the fluid level drops, the lamp switch 36 is activated to turn on the warning lamp 38.

A sensor device in accordance with the present invention in a particular blade configuration is shown in FIGS. 7 and 8. The transducer is a single bender or monomorph device. If an input electrical signal is applied across the piezoelectric layer 18 between the drive electrode 20 and the substrate 16, a mechanical force is set up across the piezoelectric layer causing the layer to bend. Since the piezoelectric material is sandwiched between the substrate and the two electrodes, the motion of the piezoelectric material is experienced by the entire assemblage. As a practical matter the blade assembly is caused to resonate by subjecting it to an electrical signal of alternating current and the resonance in turn produces an output voltage between the pickup electrode 22 and the substrate due to the presence of the piezoelectric material. The blade assembly tends to bend in an arc having a length L which is the length of the substrate 16 which projects from the base 12. The length as well as the thickness, density and Young's modulus of the blade assembly are determinative of the frequency of the resonant bending mode of the blade. Rather than have the assembly bend in an arc along its lengthwise axis, judicious selection of the ratio between the length L and the width W of the substrate with consideration being given to the support means can cause the assembly to undergo a crosswise bending mode such as is illustrated in FIG. 10 with suitable suppression of other competing mode. Care must be taken to keep the longitudinal and transverse bending modes separated or a situation can be created in which the two modes cancel each other. Under these circumstances the anticipated resonant motion will not occur and thus no output signal will be realized.

In the blade configuration, the sensor is expected to come into direct contact with the material which is being measured and therefore a barrier is required to protect the piezoelectric material particularly for certain liquid materials. For example, if the liquid is electrically conductive, direct shorting between the electrodes can occur. Also, some materials may react deleteriously with the piezoelectric itself. Therefore, a thin coating is often applied to the entire exposed surface of the blade assembly for protection thereby preventing deterioration of operating characteristics. The coating or the film must be thin enough to minimize the tendency of the coating to damp the sandwich thereby reducing or even eliminating vibration and also hard enough to avoid viscous damping which can involve energy storage in the coating. Some epoxy materials have been found particularly satisfactory in this regard. For example, in one instance the blade device was heated to approximately 300° F. and then immersed in a powdered epoxy. The device was kept in contact long enough to allow the epoxy to melt due to the preheating, and then the blade was allowed to cool in the air. A suitable protective coating of several mils usually two to three mils in thickness was formed.

Another embodiment of the blade sensor in accordance with the present invention is shown in FIG. 9. The drive electrode 20 and the pickup electrode 22 are physically arranged to produce the blade electrical characteristics which are different from those for the device shown in FIGS. 7 and 8.

Although this invention has been shown and described with respect to a preferred embodiment thereof, it should be understood by those skilled in the art that various changes and omissions in the form and detail thereof may be made therein without departing from the spirit and scope of the invention.

Having thus described a typical embodiment of my invention, that which I claim as new and desire to secure by Letters Patent of the United States is:

1. A sensor device comprising:
   a base having means for attaching the device to an object;
   a sandwich element supported by the base, capable of bending in response to an electrical input and capable of providing an electrical output in response to the bending, including:
      an electrically conductive material which forms a substrate,
      piezoelectric material, including an interbonded mixture containing phosphorous, zirconium, titanium and chromium, chemically bonded to one side of the substrate by the attachment of phosphate ions in the mixture to the substrate due to ionic bonding, a drive electrode attached to the piezoelectric material, and a pickup electrode attached to the piezoelectric material;

a first electrical conductor attached to the drive electrode; and a second electrode attached to the pickup electrode.

2. The invention according to claim 1 wherein the sandwich element has a resonant bending mode in the range of the ultrasonic frequencies.

3. The invention according to claim 2 wherein the surface area of the drive electrode is greater than the surface area of the pickup electrode.

4. The invention according to claim 3 wherein the piezoelectric material is ceramic.

5. The invention according to claim 1 wherein the piezoelectric layer is applied as a slurry coating.

6. The invention according to claim 1 wherein the base is electrically conductive.

* * * * *